US011633226B2

(12) United States Patent
Ranpura et al.

(10) Patent No.: US 11,633,226 B2
(45) Date of Patent: Apr. 25, 2023

(54) RF ELECTRODE CANNULA

(71) Applicant: Boston Scientific Neuromodulation Corporation, Valencia, CA (US)

(72) Inventors: Himanshu Ranpura, Stevenson Ranch, CA (US); Eric K. Nagaoka, Camarillo, CA (US); Patrick M. Marek, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 332 days.

(21) Appl. No.: 17/081,142

(22) Filed: Oct. 27, 2020

(65) Prior Publication Data

US 2021/0121224 A1     Apr. 29, 2021

Related U.S. Application Data

(60) Provisional application No. 62/926,683, filed on Oct. 28, 2019.

(51) Int. Cl.
*A61B 18/14* (2006.01)
*A61B 18/00* (2006.01)

(52) U.S. Cl.
CPC .... *A61B 18/14* (2013.01); *A61B 2018/00577* (2013.01); *A61B 2018/1425* (2013.01)

(58) Field of Classification Search
CPC . A61B 17/3417; A61B 17/3421; A61B 18/14; A61B 18/1477; A61B 2018/00577;

(Continued)

(56) References Cited

U.S. PATENT DOCUMENTS 5,360,009 A    11/1994  Herskovitz
5,728,143 A *   3/1998  Gough .................. A61B 18/18
                                                  606/41

(Continued)

FOREIGN PATENT DOCUMENTS

WO    2007121143 A2    10/2007
WO    2014130031 A1    8/2014

OTHER PUBLICATIONS

International Search Report and Written Opinion for the International Patent Application No. PCT/US2020/057463, dated Feb. 9, 2021, 26 pages.

(Continued)

*Primary Examiner* — Michael F Peffley
(74) *Attorney, Agent, or Firm* — Branch Partners PLLC; Bruce E. Black (57) ABSTRACT

Described herein are cannulas that comprise a cannula tube and a cannula tip. The cannula tube comprises a proximal end, a distal end, a cannula tube lumen, a sidewall, and a sidewall opening extending through the sidewall, the sidewall opening a proximal end and distal end. The cannula tip is secured to the distal end of the cannula tube and comprises a proximal tip portion that is inserted into the cannula tube lumen and a distal tip portion that extends beyond the distal end of the cannula tube. The cannula tip is configured to allow fluid to flow therethrough and is configured to eject a distal tip of an elongated device through the sidewall opening of the cannula tube as the elongated device is inserted through the cannula tube from the proximal end of the cannula tube.

20 Claims, 5 Drawing Sheets

(58) Field of Classification Search
CPC .... A61B 2018/1425; A61B 2018/1432; A61B 2018/1475; A61B 2218/002
See application file for complete search history.

(56) References Cited

U.S. PATENT DOCUMENTS

| | | | |
|---|---|---|---|
| 6,070,845 A | 6/2000 | Herskovitz | |
| 6,203,524 B1* | 3/2001 | Burney | A61B 10/0275 604/93.01 |
| 6,341,429 B1 | 1/2002 | Herskovitz | |
| 7,363,071 B2 | 4/2008 | Damasco et al. | |
| 7,725,155 B2 | 5/2010 | Dowlatshahi | |
| 7,799,024 B2* | 9/2010 | Randall | A61B 18/1477 606/41 |
| 8,512,333 B2* | 8/2013 | Epstein | A61B 18/18 606/41 |
| 8,518,037 B2 | 8/2013 | Young | |
| 8,979,830 B2 | 3/2015 | Hennings | |
| 9,717,552 B2 | 8/2017 | Cosman et al. | |
| 9,956,032 B1 | 5/2018 | Cosman et al. | |
| 10,111,703 B2 | 10/2018 | Cosman, Jr. et al. | |
| 10,136,937 B1 | 11/2018 | Cosman, Jr. et al. | |
| 10,136,942 B1 | 11/2018 | Cosman, Jr. et al. | |
| 10,136,943 B1* | 11/2018 | Cosman, Jr. | A61B 18/1482 |
| 10,194,971 B2 | 2/2019 | Wegrzyn, III et al. | |
| 10,342,606 B2 | 7/2019 | Cosman et al. | |
| 10,363,063 B2 | 7/2019 | Cosman | |
| 10,548,654 B2 | 2/2020 | Curley | |
| 10,588,687 B2 | 3/2020 | Cosman, Jr. et al. | |
| 10,631,915 B1 | 4/2020 | Cosman | |
| 10,639,098 B2 | 5/2020 | Cosman et al. | |
| 10,639,101 B2 | 5/2020 | Cosman et al. | |
| 2002/0077683 A1 | 6/2002 | Westlund et al. | |
| 2005/0065509 A1 | 3/2005 | Coldwell et al. | |
| 2005/0277918 A1* | 12/2005 | Shah | A61N 1/06 606/41 |
| 2010/0222747 A1 | 9/2010 | Wenchell et al. | |
| 2011/0288540 A1 | 11/2011 | Wright et al. | |
| 2014/0066917 A1 | 3/2014 | Cosman, Jr. et al. | |
| 2014/0081260 A1 | 3/2014 | Cosman, Jr. et al. | |
| 2014/0121658 A1 | 5/2014 | Cosman, Jr. et al. | |
| 2015/0305799 A1 | 10/2015 | Trieu | |
| 2016/0278791 A1 | 9/2016 | Pellegrino et al. | |
| 2017/0004951 A1 | 1/2017 | Weisz et al. | |
| 2017/0049514 A1 | 2/2017 | Cosman | |
| 2020/0038091 A1 | 2/2020 | Cao et al. | |
| 2020/0330153 A1 | 10/2020 | Cosman, Jr. et al. | |
| 2021/0121224 A1 | 4/2021 | Ranpura et al. | |
| 2021/0236191 A1 | 8/2021 | Wang et al. | |

OTHER PUBLICATIONS

"Venom cannula and electrode system"—Stryker—retrieved Sep. 8, 2020 URL: https://www.stryker.com/us/en/interventional-spine/products/venom-cannula-and-electrode-system.html.

"RF Trident™ Cannulae" Diros Technology Inc. Nov. 11, 2017 URL: https://web.archive.org/web/20171117054945/https://dirostech.com/product-details/rf-tridenttndent-hybrid-cannulae/.

Cedeno et al., "Comparisons of Lesion Volumes and Shapes Produced by a Radiofrequency System with a Cooled, a Protruding, or a Monopolar Probe" Pain Physician 2017; 20:E915-E922 • ISSN 2150-1149.

Correspondence from Department of Health and Human Services to George Darmos at Diros Technology, Inc.—dated Jul. 30, 2015—11 pages.

Correspondence from Department of Health and Human Services to Christina McKee—dated Mar. 28, 2013—07 pages.

Hemostasis Vales—Qosina—URL: hllps://www.qosina.com/vascular-access-hemostasis-valves 9 pages—retrieved Nov. 13, 2019.

Coolief Cooled Radio Frequency Kit—Instructions for Use Halyard—dated Feb. 9, 2017—8 pages.

Cobra R-F™—Epimed—URL: https://www.epimed.com/products/cobra-r-f/—retrieved Jan. 27, 2021.

Hyso et al., "Epimed Launches "Cobra" R-F™ Dual Use Radiofrequency Cannula" Cision—PR Web—Jan. 17, 2019 3 pages.

U.S. Appl. No. 63/130,519, filed Dec. 24, 2020.

U.S. Appl. No. 63/131,260, filed Dec. 28, 2020.

Written Opinion of the International Preliminary Examining Authority received for PCT Application No. PCT/US2020/057463 dated Oct. 4, 2021.

International Preliminary Report on Patentability for PCT Application No. PCT/US2020/057463 dated Jan. 21, 2022.

U.S. Appl. No. 63/138,092, filed Jan. 15, 2021.

* cited by examiner

RF ELECTRODE CANNULA

CROSS-REFERENCE TO RELATED APPLICATION

This application claims the benefit of U.S. Provisional Application No. 62/926,683, filed Oct. 28, 2019 and entitled "RF ELECTRODE CANNULA", the entire contents of which are herein incorporated by reference.

FIELD

The present disclosure pertains to novel cannulas and to systems and methods that employ such cannulas.

BACKGROUND

Cannula and electrode assemblies are known and have been used for some time for tissue ablation. Among these are cannula and electrode assemblies in which the cannula is provided with a side opening a short distance away from the distal tip of the cannula through which the electrode is guided such that the distal tip of the electrode extends out of the side opening. When current is supplied to such an assembly, ablation current flows through a volume larger than would otherwise be affected by an assembly in which the electrode extends out of the distal end of the cannula.

SUMMARY

In some aspects, the present disclosure pertains to cannulas that comprise (a) a cannula tube comprising a proximal end, a distal end, a cannula tube lumen, a sidewall, and a sidewall opening extending through the sidewall, the sidewall opening having a proximal end and distal end and (b) a cannula tip secured to the distal end of the cannula tube, the cannula tip comprising a proximal tip portion that is inserted into the cannula tube lumen and a distal tip portion that extends beyond the distal end of the cannula tube, the cannula tip being configured to allow fluid to flow therethrough, and the cannula tip being configured to eject a distal tip of an elongated device through the sidewall opening as the elongated device is inserted through the cannula tube from the proximal end of the cannula tube.

In some embodiments, the cannula tip is secured to the cannula tube by a weld.

In some embodiments, which can be used in conjunction of any of the above aspects and embodiments, the distal end of sidewall opening is beveled.

In some embodiments, which can be used in conjunction of any of the above aspects and embodiments, the sidewall opening extends around a circumference of the cannula tube by and angle ranging from 120 to 160 degrees, In some embodiments, which can be used in conjunction of any of the above aspects and embodiments, the cannula tube is bent at proximal end of the sidewall opening by an angle ranging from 5 to 45 degrees.

In some embodiments, which can be used in conjunction of any of the above aspects and embodiments, the proximal tip portion has a first outer diameter and the distal tip portion has a second outer diameter that is larger than the first outer diameter, and there is a step-up in diameter between the proximal tip portion and the distal tip portion such that the proximal tip portion is inserted into a distal end of the cannula tube and such that the proximal end of the distal tip portion abuts the distal end of the cannula tube portion.

In some embodiments, which can be used in conjunction of any of the above aspects and embodiments, the distal tip portion has an outer diameter that is the same as an outer diameter of the cannula tube.

In some embodiments, which can be used in conjunction of any of the above aspects and embodiments, the cannula tip comprises a lumen that allows fluid to flow therethrough, a channel that allows fluid to flow therethrough, a slot that allows fluid to flow therethrough, a combination of a lumen and a slot that allow fluid to flow therethrough, a combination of a lumen and a channel that allow fluid to flow therethrough, a combination of a channel and a slot that allow fluid to flow therethrough, or a combination of a lumen, a channel and a slot that allow fluid to flow therethrough.

In some embodiments, which can be used in conjunction of any of the above aspects and embodiments, the proximal tip portion comprises a slot and the distal tip portion comprises a distal tip lumen in fluid communication with the slot.

In some embodiments, which can be used in conjunction of any of the above aspects and embodiments, the proximal portion of the cannula tip comprises a ramp at a proximal end thereof, the ramp having a proximal end and a distal end. In some of these embodiments, the slot bisects the ramp and/or the distal end of the ramp terminates proximal to the distal end of the sidewall opening.

In some embodiments, which can be used in conjunction of any of the above aspects and embodiments, the slot does not extend to the distal end of the proximal tip portion.

In some embodiments, which can be used in conjunction of any of the above aspects and embodiments, the distal end of the slot comprises a circular recess that is axially aligned with and has same diameter as the distal tip lumen.

In some embodiments, which can be used in conjunction of any of the above aspects and embodiments, the cannula further comprises a hub that is attached to the proximal end of the cannula tube.

In some aspects, the present disclosure further provides a system that comprises: (a) a cannula in accordance with any of the above aspects and embodiments and (b) an electrode having a distal electrode tip, wherein the electrode is configured to be inserted into a proximal end of the cannula and through the cannula tube, and wherein the cannula tip is configured to eject the distal electrode tip through the sidewall opening of the cannula tube as the electrode is inserted through the cannula tube from the proximal end of the cannula. In some embodiments, the distal electrode tip is rounded.

In some aspects, the present disclosure further provides an assembly that comprises: (a) a cannula in accordance with any of the above aspects and embodiments and (b) a stylet having a stylet tip, wherein the stylet is configured to be inserted into a proximal end of the cannula and through the cannula tube such that the stylet tip is proximate the sidewall opening when fully inserted.

In some embodiments, the cannula further comprises a hub that is attached to the proximal end of the cannula tube, wherein the stylet comprises a stylet cap that is attached to a proximal end of the stylet. In some of these embodiments, the stylet cap engages the cannula hub.

These and other aspects, embodiments and advantages of the present disclosure will become immediately apparent to those of ordinary skill in the art upon review of the detailed description and claims to follow.

DETAILED DESCRIPTION

As discussed in more detail below, in one aspect, the present disclosure pertains to cannulas that are useful for guiding an elongated internal device such that the elongated internal device is ejected through a sidewall opening in the cannulas instead of extending through a distal end of the cannulas. In various embodiments described herein, the elongated internal device is an RF electrode. However, it should be understood that the cannulas described herein may be used in systems that include internal devices other than RF electrodes.

Cannulas in accordance with the present disclosure include (a) a cannula tube comprising a proximal end, a distal end, a cannula tube lumen, a sidewall and a sidewall opening extending through the sidewall and (b) a cannula tip secured to a distal end of the cannula tube, the cannula tip having proximal tip portion that is inserted into the cannula tube lumen and a distal tip portion extending beyond the distal end of the cannula tube. The cannula tip is configured to allow fluid to flow through the cannula tip and is also configured to eject a distal tip of an elongated device (e.g., an electrode) through the sidewall opening as the device is inserted through the cannula tube from a proximal end of the cannula tube. In this way, the cannulas of the present disclosure allow fluid that is injected though the lumen of the cannula tube to be dispensed from a distal end of the cannula while at the same time disallowing the electrode from proceeding past the side port to the distal end of the cannula.

Figure 1:
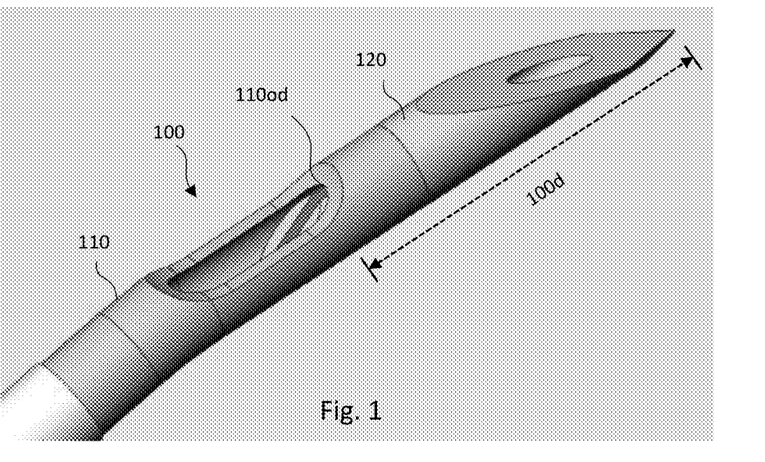
FIG. 1 is a schematic illustration of a distal end of a cannula, in accordance with an embodiment of the present disclosure.
Figure 2:
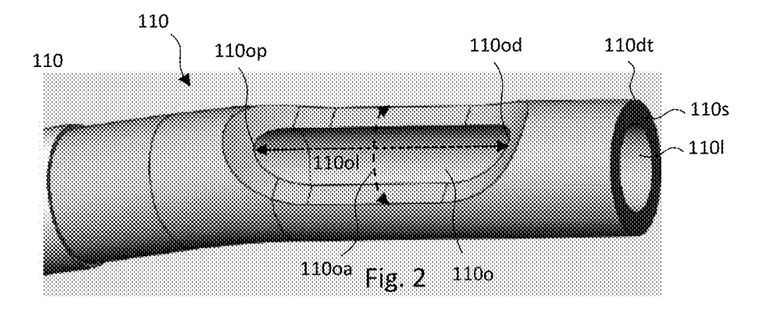
FIG. 2 is a schematic illustration of a distal end of a cannula tube, in accordance with an embodiment of the present disclosure.
Figure 3:
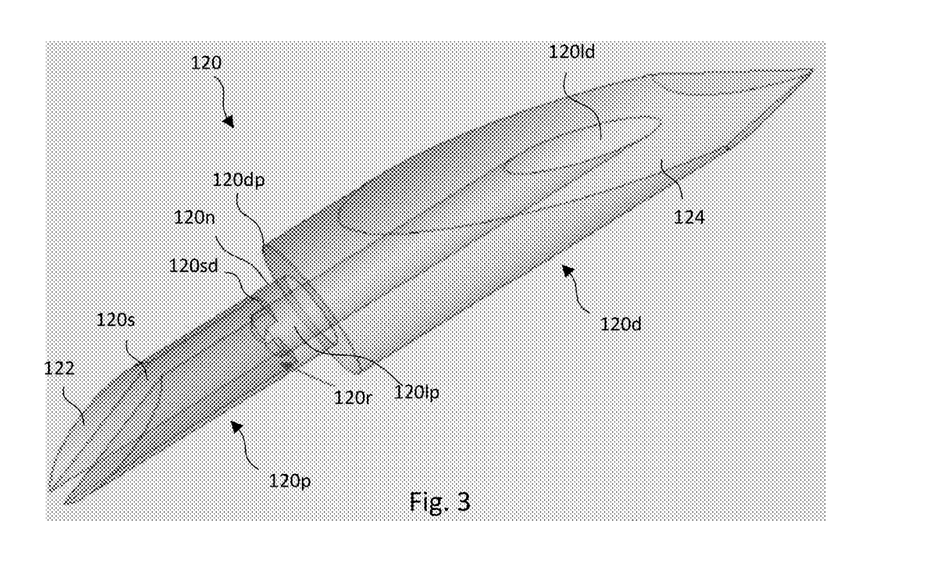
FIG. 3 is a schematic illustration of a cannula tip, in accordance with an embodiment of the present disclosure.

With reference now to the drawings, a cannula 100 in accordance with the present disclosure is shown in FIG. 1. The cannula shown in FIG. 1 is formed from a cannula tube 110 as shown in FIG. 2 and a cannula tip 120 as shown in FIG. 3. A variety of materials may be used to form the cannula tube 110 and cannula tip 120, including various metallic and polymer materials.

Turning now to FIG. 2 (also seen, for example, in FIGS. 4A-4B), a distal portion of a cannula tube 110 in accordance with an embodiment of the present disclosure is schematically illustrated therein. The cannula tube 110 includes a cannula tube lumen 110*l*, a sidewall 110*s*, and a sidewall opening 110*o* having a proximal end 110*op* and distal end 110*od*. The outer diameter of the cannula tube will vary widely, depending on the application, and may range, for example, between 16 gauge (1.651 mm) and 23 gauge (0.6414 mm), among other values. The thickness of the sidewall 110*s* and the diameter of the inner lumen 110*l* will depend on the gauge selected. Typically sidewall 110*s* thickness may range from 0.229 mm (e.g., for a 16 gauge regular wall) to 0.102 mm (e.g., for a 23 gauge thin wall), among other values. Typically, the diameter of the inner lumen 110*l* ranges may range from 1.194 mm (e.g., for a 16 gauge regular wall) to 0.432 mm (e.g., for a 23 gauge thin wall), among other values. The length 110*ol* of the sidewall opening will also vary depending on the gauge selected. In some embodiments, the length 110*ol* of the sidewall opening may range, for example, from 1.5 mm to 4.0 mm, for example 2.425 mm (based on a 18 gauge prototype) to 2.88 mm (based on a 20 gauge prototype), among other values.

The sidewall opening 110*o* will extend around a circumference of the cannula tube 110 by various angles 110*oa*, extending, for example, from 45 to 240 degrees, preferably from 100 to 180 degrees, more preferably from 120 to 160 degrees, around a circumference of the cannula tube 110, among other values.

The sidewall opening 110*o* may be formed by any suitable process, including machining, wire EDM, grinding, or laser cutting. Once formed, the edges of the sidewall opening 110*o* may be beveled via grinding and/or an electropolishing process. In various embodiments, the distal end 110*od* of the sidewall opening 110*o* may be provided with a bevel angle that matches an angle of a ramp of the cannula tip 120 (described below).

In certain embodiments, a distal end of the cannula tube 110 may be bent at an angle 110*a* (see FIG. 4B) to assist with the expulsion of the electrode. For example, the cannula tube 110 may be bent at an angle 110*a* ranging, from 5 to 45 degrees, typically ranging from 10 to 30 degrees, among other values.

In particular embodiments, the materials for cannula tube 110 may be formed from metallic materials including iron-chromium alloys, such as stainless steel, nickel-titanium alloys, such as nitinol, and nickel-chromium alloys, such as inconel.

Turning now to FIG. 3 (see also FIGS. 4A-4B), a cannula tip 110 in accordance with an embodiment of the present disclosure is schematically illustrated. The cannula tip 120 has a proximal end 110*p* and a distal end 110*d*. The cannula tip 120 is configured to allow fluid flow therethough as discussed in more detail below. The cannula tip 120 also comprises a ramp 122 at a proximal portion 120*p* thereof that is configured to assist with expelling an internal device such as an electrode from the sidewall opening 110*o* of the cannula 100, by nudging a tip of the electrode in a direction of the sidewall opening 110*o*. In certain embodiments, a proximal face of the ramp is provided with a ramp angle 122*a* (see FIG. 4B) relative to a longitudinal axis of the cannula tip 120. For example, the ramp 122 may be provided with a ramp angle 122*a* ranging, for example, from 15 to 60 degrees, typically ranging from 25 to 35 degrees, among other values.

Moreover, the cannula tip 120 typically comprises a bevel 124 at a distal tip thereof that is configured to enhance the ability of the cannula 100 to pierce tissue.

In particular embodiments, the materials for cannula tip 120 may be formed from metallic materials including iron-chromium alloys such as stainless steel, nickel-titanium alloys such as nitinol, and nickel-chromium alloys such as inconel.

As seen from FIG. 1, upon assembly of the cannula tube 110 and the cannula tip 120, the distal end 110od of the sidewall opening 110o will be a predetermined distance 100d from the distal-most tip of the cannula tip 120. In some embodiments, the distance 100d may range from 2 to 10 mm.

In the embodiment shown, the cannula tip 120 mates with the distal tip 110dt of the cannula tube 110. In order to provide this feature, a proximal portion 120p of the cannula tip 120 is formed such that a diameter of the proximal portion 120p is less than an inner diameter of the cannula tube 110 (i.e., the diameter of the lumen 110l) at a distal end of the cannula tube 110d, such that that the proximal portion 120p of the cannula tip 120 can be inserted into the distal end 110d of the cannula tube 110.

In various embodiments, a distal portion 120d of the cannula tip 120 is formed with a diameter that is greater than an inner diameter of the cannula tube 110 (i.e., the diameter of the lumen 110l) at a distal end 110d of the cannula tube 110. In other words, there is a step-up in the diameter of the cannula tip 120 at a point where the distal portion 120d of the cannula tip 120 transitions to the proximal portion 120p of the cannula tip 120. In this way, the proximal portion 120p of the cannula tip 120 can be inserted into the distal 120d of cannula tube 110, but only to a point where a proximal tip 120dp of the distal portion 120d of the cannula tip 120 abuts the distal tip 110dt of the cannula tube 110. In various embodiments, an outer diameter at the proximal tip 120dp of the distal portion 120d matches an outer diameter of the cannula tube 110 at a distal tip 110dt of the cannula tube 110.

The cannula tip 120 may be secured to the distal end 110d of the cannula tube 110 by a variety of methods including, for example, by welding (e.g., laser welding) by friction fit, of by use of a suitable adhesive, among other methods.

As previously noted, in various embodiments, cannulas 100 in accordance with the present disclosure are configured are configured to allow fluid to flow therethough, such that fluid flows from a distal end of the cannulas 100. As an initial matter, it is noted that in order to provide the cannulas described herein with this feature, some mechanism must be provided to allow for fluid to flow through and/or around the cannula tip 120. The present inventors have developed various strategies for providing the cannulas described herein with this feature, including lumens, channels, slots, and combination of these features.

Figure 6:
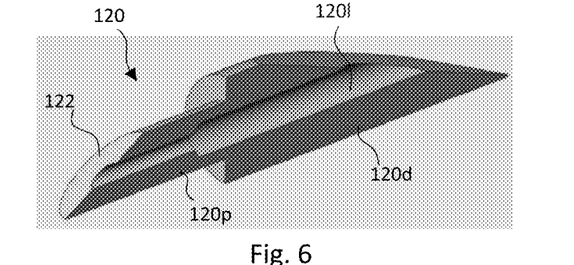
FIG. 6 is a schematic illustration of a cannula tip, in accordance with an embodiment of the present disclosure.

For example, referring to FIG. 6, in one embodiment, a cannula tip 120 is provided having a lumen 120l extending therethrough. Although the lumen 120l shown has an increase in diameter between the proximal portion 120p of the cannula tip 120 and the distal portion 120d of the cannula tip 120, other designs are possible in which the lumen 120l decreases in diameter between the proximal portion 120p of the cannula tip 120 and the distal portion 120d of the cannula tip 120, or in which the lumen 120l is of constant diameter within the proximal portion 120p of the cannula tip 120 and the distal portion 120d of the cannula tip 120.

Figure 7:
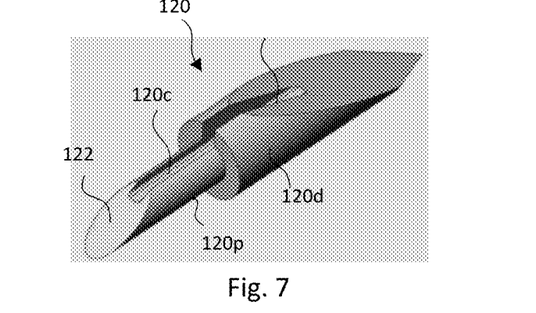
FIG. 7 is a schematic illustration of a cannula tip, in accordance with another embodiment of the present disclosure.

As another example, as seen in FIG. 7, a cannula tip 120 may be provided that has a channel 120c extending along the proximal portion 120p of the cannula tip 120 and the distal portion 120d of the cannula tip 120.

Figure 8:
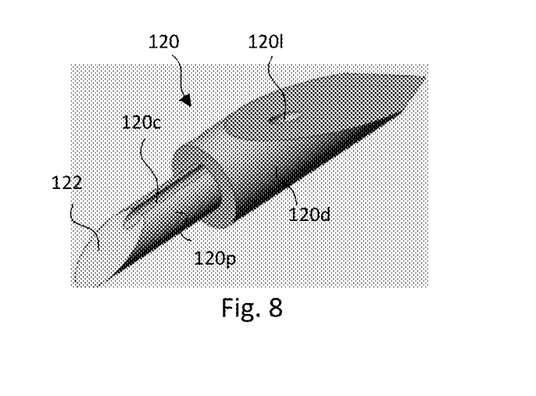
FIG. 8 is a schematic illustration of a cannula tip, in accordance with yet an embodiment of the present disclosure.
Figure 9A:
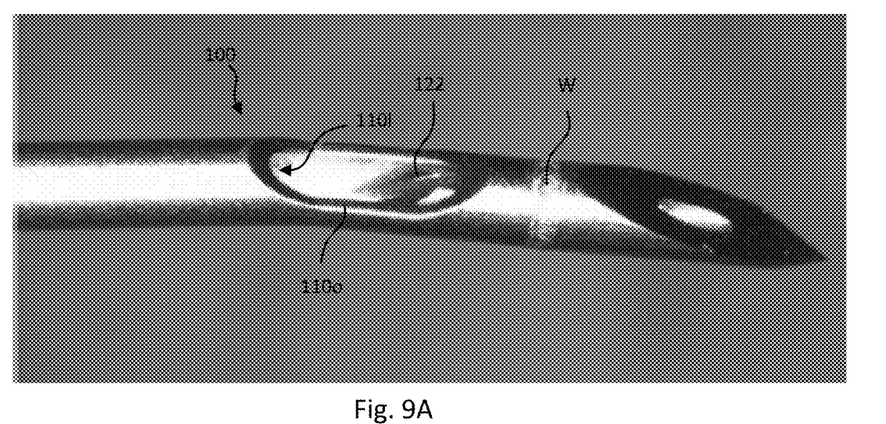
FIGS. 9A-9C are photographic images of a system that includes a cannula and an electrode, in accordance with an embodiment of the present disclosure, at various points of advancement of the electrode within the cannula.
Figure 9B:
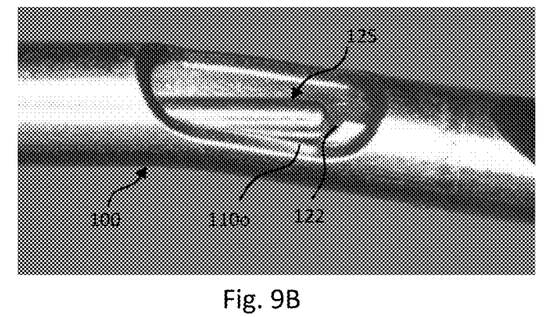
Figure 9C:
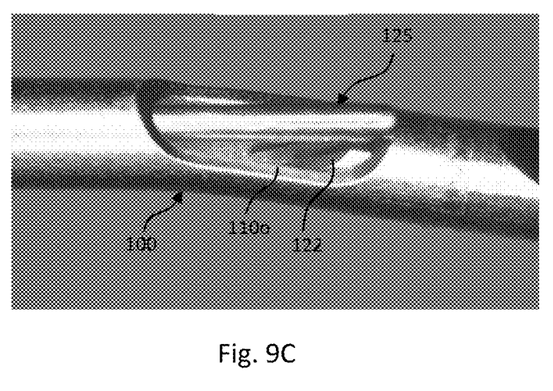

As another example, as seen in FIG. 8, a cannula tip 120 may be provided that has a channel 120c within the proximal portion 120p of the cannula tip 120 and a lumen 120l within the distal portion 120d of the cannula tip 120.

In other embodiments shown in FIGS. 1, 3, 4A, 4B and 5, a cannula tip 120 may be provided having a slot 120s within the proximal portion 120p of the cannula tip 120 and a lumen 120ld in the distal portion 120p of the cannula tip 120. It is noted that the slot 120s in FIG. 5 extends along the entire length of the proximal portion 120p of the cannula tip 120 (i.e., all the way to the proximal tip 120dp of the distal portion 120d of the cannula tip 120 where there is a step-up in the diameter of the cannula tip 120).

Figure 4A:
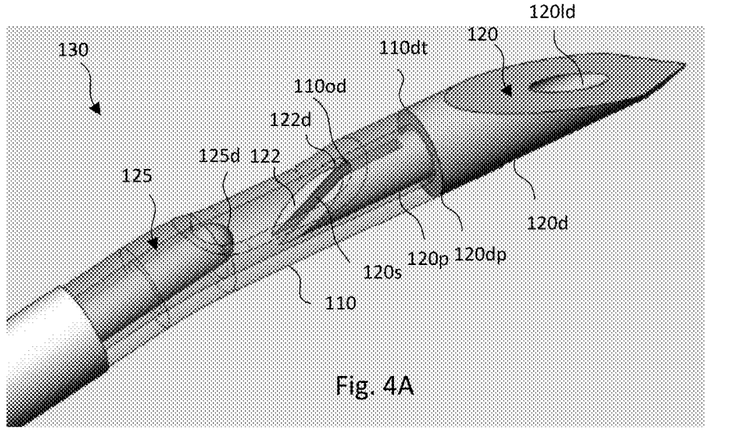
FIGS. 4A and 4B are schematic illustrations of a distal end of a system that includes a cannula and an electrode, in accordance with an embodiment of the present disclosure.
Figure 4B:
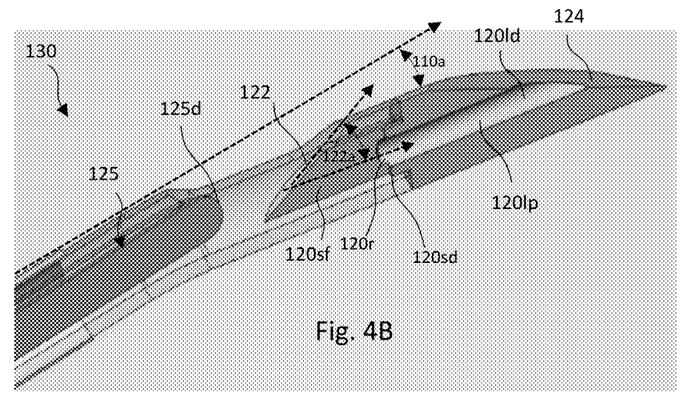

In FIGS. 3, 4A-4B, on the other hand, the slot 120 does not extend all the way to the proximal tip 120dp of the distal portion 120d (i.e., the slot 120s terminates at a point proximal to the step-up in the diameter of the cannula tip 120). Consequently, the proximal portion 120p of the cannula tip 120 contains a section of lumen 120lp, which opens into the slot 120s and which is an extension of the lumen 120ld in the distal portion 120p of the cannula tip 120. In other embodiments (not shown), the slot 120s may only extend the axial length of the ramp 122. A potential advantage of terminating the slot 120s at a point proximal to the step-up in the diameter of the cannula tip 120 is that potential issues may be avoided that can arise when the cannula tip 120 is welded to the cannula tube 110.

As can be further seen from FIGS. 3 and 4B, in the design shown, a circular recess 120r is formed at the distal end of the slot 120s, which is is axially aligned with and has same diameter as the lumen 120lp/120ld.

In certain embodiments, cannula tips 120 in accordance with the present disclosure can be machined from a solid rod of material, for example, by drilling a hole in a distal end of the material, forming a bevel in the distal end of the material, reducing a diameter of the proximal end of the material, grinding a ramp in the proximal end of the material, and forming a slot in the proximal end of the material.

Figure 5:
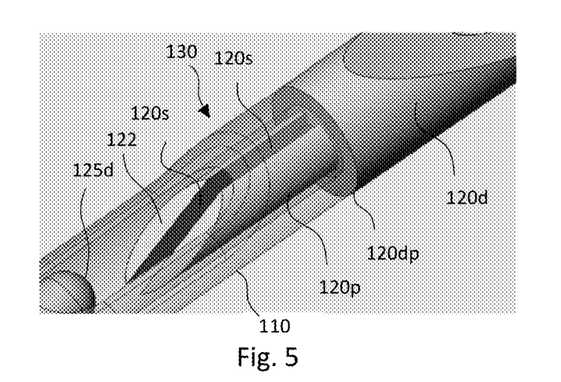
FIG. 5 is a schematic illustration of a distal end of a system that includes a cannula and an electrode, in accordance with another embodiment of the present disclosure.

As can be seen, for example, from FIGS. 1, 4A and 5, a length of the proximal portion 120p of the cannula tip 120 is beneficially dimensioned such that, upon insertion of the proximal portion 120p of the cannula tip 120 into the distal end 110d of the cannula tube 110, the ramp 122 is positioned such that a distal end 122d of the ramp 122 lies at or just proximal to the distal end 110od of the sidewall opening 110o (see, e.g., FIG. 4A). Moreover, as noted above, the distal end 110od of the sidewall opening 110o may be beveled at an angle that approximately matches the angle of the ramp 122, in certain beneficial embodiments.

Figures 10A, 10B:
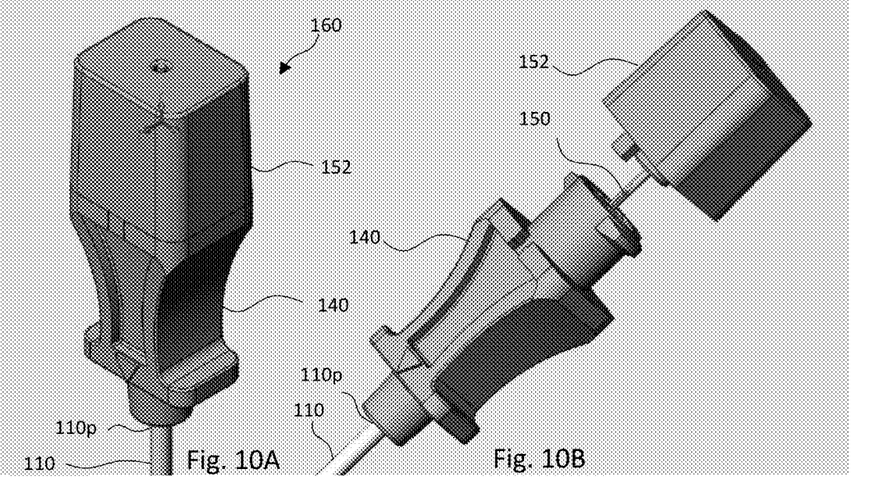
FIGS. 10A-10C are schematic illustrations of an assembly that comprises a cannula with a cannula hub and a stylet with a stylet cap, in accordance with an embodiment of the present disclosure.
Figure 10C:
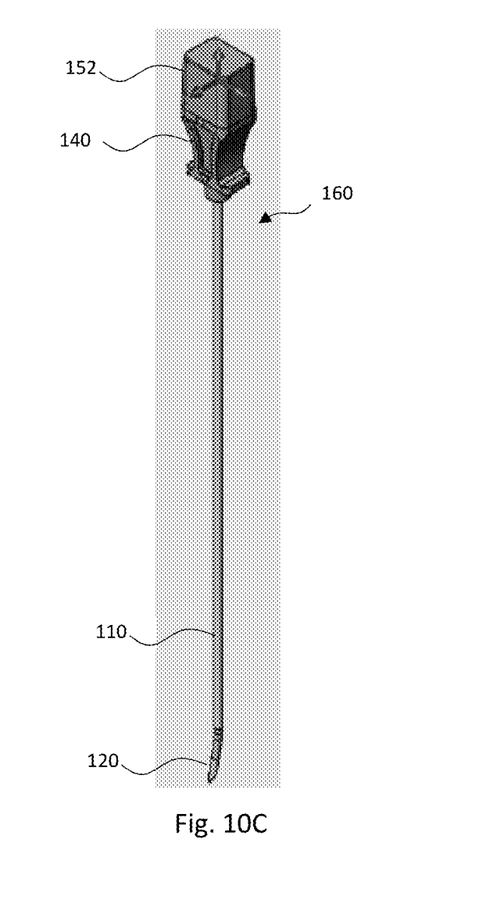

Turning now to FIGS. 10A-10C, in various embodiments, cannulas 100 in accordance with the present disclosure may be provided with a cannula hub 140, which is attached to a proximal end 110p of the cannula tube 110. In various embodiments, an assembly 160 may be provided which further includes a stylet 150 having a stylet cap 152. The stylet 150 may be inserted into the cannula hub 140 and cannula tube 110 of a cannula 100 in accordance with the present disclosure. Moreover the stylet cap 152 can be configured to engage with the cannula hub 140 as shown. Materials for forming the stylet cap 152 and cannula hub 140 include any suitable material, with plastics, for example, acrylic polymers and polycarbonate being particularly beneficial in some embodiments. Materials for forming the stylet 150 include polypropylene, polycarbonate, acrylonitrile butadiene styrene (ABS), and ABS/polycarbonate blends. The stylet 150 can provide structural rigidity to the cannula 100 during insertion into a patient. Moreover, by having a distal tip of the stylet 150 terminate at (but not extend from) the sidewall opening 110*o*, coring of tissue during insertion of the cannula 100 can be reduced or prevented.

Turing now to the embodiments shown schematically in FIGS. 4A, 4B, 5, and 9A-9C, in some aspects, the present disclosure provides systems that include a cannula 100 in accordance with the disclosure and an electrode 125 this is insertable into the cannula 100. In certain of these embodiments, the electrode 125 is provided with a rounded (e.g., hemispherical) distal tip 125*d*. In certain of these embodiments, the electrode 125 is straight with no bend. Materials for forming the electrode 125 include metals and metal alloys as stainless steel, Inconel, or nitinol.

In some embodiments the electrode 125 can be operated in unipolar fashion, for example, in conjunction with one or more return electrodes positioned on a patient's body. In some embodiments, the electrode 125 can be operated in a bipolar fashion, for example, with a distal tip 120 of the cannula 100 acting as the other member of the bipolar pair, in which case the electrode 125 and/or cannula 100 will be suitably insulated to avoid shorting the electrode 125 and cannula 100.

When the distal tip 125*d* of an electrode 125 that has been inserted through a cannula tube 110 from a proximal end of a cannula 100 in accordance with the present disclosure (e.g., by being inserted through a hub 140 like that shown in FIGS. 10A-10C at a proximal end 110*p* of the cannula tube 110) has traveled though the cannula tube 110 to a point where the distal tip 125*d* reaches the ramp 122 of the cannula tip 120, the ramp 122 acts to deflect the electrode distal tip 125*d* out through the sidewall opening 110*o* of the cannula tube 110, rather than allowing the electrode distal tip 125*d* of the electrode 125 to continue traveling into the cannula tip 120. In these embodiments, the width of the electrode 125 is narrower than the width of the cannula tube 110 lumen 110*l* and is wider than the slot that is formed in the ramp 122 (or the channel or hole that is formed in the ramp 122 in other embodiments). In this regard, a top view of a cannula 100 in accordance with the present disclosure is illustrated FIG. 9A, in which can be seen the sidewall opening 110*o* of the cannula tube 110 and the ramp 122 of the inserted cannula tip 120. A weld W securing the cannula tip 120 to the cannula tube 110 can be seen in the right-hand portion of the photograph. As seen from FIGS. 9B and 9C, when an electrode 125 that has been inserted into a proximal end of the cannula 100 reaches the ramp 122, the ramp acts to deflect the distal tip 125*d* of the electrode 125 out through the sidewall opening 110*o* of the cannula tube 110.

In some embodiments, the system is further provided with a container of fluid for injection, for example, a container of anesthetic fluid, saline, contrast media (including radiopacity fluid), dye-containing fluid, or steroid-containing fluid. For example, injection fluid can be provided in a syringe that is engageable with the cannula hub 140. As noted above, the cannula designs of the present disclosure are advantageous in that they allow fluid that is injected though the lumen of the cannula tube to be dispensed from a distal end of the cannula while at the same time preventing an inserted electrode to proceed beyond the side port to the distal end of the cannula.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A cannula comprising (a) a cannula tube comprising a proximal end, a distal end, a cannula tube lumen, a sidewall, and a sidewall opening extending through the sidewall, the sidewall opening having a proximal end and distal end and (b) a cannula tip secured to the distal end of the cannula tube, the cannula tip comprising a proximal tip portion that is inserted into the cannula tube lumen and a distal tip portion that extends beyond the distal end of the cannula tube, the cannula tip being configured to allow fluid to flow therethrough, wherein the proximal tip portion of the cannula tip comprises a ramp at a proximal end thereof, wherein the ramp is configured to eject a distal tip of an elongated device through the sidewall opening of the cannula tube as the elongated device is inserted through the cannula tube from the proximal end of the cannula tube.

2. The cannula of claim 1, wherein the cannula tip is secured to the cannula tube by a weld.

3. The cannula of claim 1, wherein the distal end of the sidewall opening is beveled.

4. The cannula of claim 1, wherein the sidewall opening extends around a circumference of the cannula tube by an angle ranging from 120 to 160 degrees.

5. The cannula of claim 1, wherein the cannula tube is bent at the proximal end of the sidewall opening by an angle ranging from 5 to 45 degrees.

6. The cannula of claim 1, wherein the proximal tip portion has a first outer diameter and the distal tip portion has a second outer diameter that is larger than the first outer diameter, and wherein there is a step-up in diameter between the proximal tip portion and the distal tip portion such that the proximal tip portion is inserted into the distal end of the cannula tube and such that the proximal end of the distal tip portion abuts the distal end of the cannula tube.

7. The cannula of claim 1, wherein the distal tip portion has an outer diameter that is the same as an outer diameter of the cannula tube.

8. The cannula of claim 1, wherein the cannula tip comprises a lumen that allows fluid to flow therethrough, a channel that allows fluid to flow therethrough, a slot that allows fluid to flow therethrough, a combination of a lumen and a slot that allow fluid to flow therethrough, a combination of a lumen and a channel that allow fluid to flow therethrough, a combination of a channel and a slot that allow fluid to flow therethrough, or a combination of a lumen, a channel and a slot that allow fluid to flow therethrough.

9. The cannula of claim 1, wherein the proximal tip portion comprises a slot and the distal tip portion comprises a distal tip lumen in fluid communication with the slot.

10. The cannula of any claim 9, wherein the slot bisects the ramp.

11. The cannula of claim 9, wherein the slot does not extend to the distal end of the proximal tip portion.

12. The cannula of claim 9, wherein the distal end of the slot comprises a circular recess that is axially aligned with and has a same diameter as the distal tip lumen.

13. The cannula of claim 1, wherein the ramp has a proximal end and a distal end and the distal end of the ramp terminates proximal to the distal end of the sidewall opening.

14. The cannula of claim 1, wherein the cannula further comprises a hub that is attached to the proximal end of the cannula tube.

15. The cannula of claim 1, wherein the cannula tip comprises at least one of i) a channel that allows fluid to flow therethrough or ii) a slot that allows fluid to flow therethrough.

16. A system comprising:
a cannula comprising (a) a cannula tube comprising a proximal end, a distal end, a cannula tube lumen, a sidewall, and a sidewall opening extending through the sidewall, the sidewall opening having a proximal end and distal end and (b) a cannula tip secured to the distal end of the cannula tube, the cannula tip comprising a proximal tip portion that is inserted into the cannula tube lumen and a distal tip portion that extends beyond the distal end of the cannula tube, the cannula tip being configured to allow fluid to flow therethrough, wherein the proximal tip portion of the cannula tip comprises a ramp at a proximal end thereof, wherein the ramp is configured to eject a distal tip of an elongated device through the sidewall opening of the cannula tube as the elongated device is inserted through the cannula tube from the proximal end of the cannula tube; and
an electrode having a distal electrode tip, wherein the electrode is configured to be inserted into the proximal end of the cannula tube and through the cannula tube, and wherein the cannula tip is configured to eject the distal electrode tip through the sidewall opening of the cannula tube as the electrode is inserted through the cannula tube from the proximal end of the cannula tube.

17. The system of claim 16, wherein the distal electrode tip is rounded.

18. An assembly comprising:
a cannula comprising (a) a cannula tube comprising a proximal end, a distal end, a cannula tube lumen, a sidewall, and a sidewall opening extending through the sidewall, the sidewall opening having a proximal end and distal end and (b) a cannula tip secured to the distal end of the cannula tube, the cannula tip comprising a proximal tip portion that is inserted into the cannula tube lumen and a distal tip portion that extends beyond the distal end of the cannula tube, the cannula tip being configured to allow fluid to flow therethrough, wherein the proximal tip portion of the cannula tip comprises a ramp (122) at a proximal end thereof, wherein the ramp is configured to eject a distal tip of an elongated device through the sidewall opening of the cannula tube as the elongated device is inserted through the cannula tube from the proximal end of the cannula tube; and
a stylet having a stylet tip, wherein the stylet is configured to be inserted into the proximal end of the cannula tube and through the cannula tube such that the stylet tip is proximate the sidewall opening when fully inserted.

19. The assembly of claim 18, wherein the cannula further comprises a hub that is attached to the proximal end of the cannula tube, wherein the stylet comprises a stylet cap that is attached to a proximal end of the stylet.

20. The assembly of claim 19, wherein the stylet cap is configured to engage the cannula hub.

* * * * *